(12) United States Patent
Kuriki et al.

(10) Patent No.: US 10,973,540 B2
(45) Date of Patent: Apr. 13, 2021

(54) ENDOSCOPIC SURGICAL DEVICE

(71) Applicants: OLYMPUS CORPORATION, Hachioji (JP); Haruhiro Inoue, Yokohama (JP)

(72) Inventors: Hiroki Kuriki, Tokyo (JP); Haruhiro Inoue, Kanagawa (JP)

(73) Assignees: OLYMPUS CORPORATION, Tokyo (JP); Haruhiro Inoue, Yokohama (JP)

( * ) Notice: Subject to any disclaimer, the term of this patent is extended or adjusted under 35 U.S.C. 154(b) by 210 days.

(21) Appl. No.: 16/046,465

(22) Filed: Jul. 26, 2018

(65) Prior Publication Data

US 2018/0368869 A1 Dec. 27, 2018

Related U.S. Application Data

(63) Continuation of application No. PCT/JP2016/053106, filed on Feb. 2, 2016.

(51) Int. Cl.
*A61B 17/29* (2006.01)
*A61B 17/00* (2006.01)
(Continued)

(52) U.S. Cl.
CPC .......... *A61B 17/29* (2013.01); *A61B 1/00135* (2013.01); *A61B 1/015* (2013.01);
(Continued)

(58) Field of Classification Search
CPC ............ A61B 2017/2929; A61B 10/06; A61B 2017/1125; A61B 17/2804;
(Continued)

(56) References Cited

U.S. PATENT DOCUMENTS 6,066,102 A 5/2000 Townsend et al.
6,183,469 B1 2/2001 Thapliyal et al.
(Continued)

FOREIGN PATENT DOCUMENTS

EP 1726266 A1 11/2006
EP 1752108 A1 2/2007
(Continued)

OTHER PUBLICATIONS

Sep. 20, 2017 Japanese Office Action issued in Patent Application No. 2017-526712.
(Continued)

*Primary Examiner* — Wade Miles
(74) *Attorney, Agent, or Firm* — Oliff PLC (57) ABSTRACT

Provided is an endoscopic surgical device includes: a sheath having a pipe for delivering a liquid and inserted into a channel of an endoscope; a pair of forceps components disposed so as to protrude from a distal end cover of the sheath; an operable member that is connected to the forceps components and opens and closes the forceps components; and a flow-path formation member positioned at proximal end side rather than the forceps components and is disposed in a rotatable manner about a central axis of the sheath together with the forceps components. The flow-path formation member includes a recess disposed in a direction orthogonal to an opening-closing direction of the forceps components and recessed radially inward. The recess forms a gap between the flow-path formation member and an inner peripheral surface of the distal end cover so as to constitute a liquid delivery hole.

14 Claims, 7 Drawing Sheets

(51) Int. Cl.
 *A61B 18/14* (2006.01)
 *A61B 1/00* (2006.01)
 *A61B 1/015* (2006.01)
 *A61B 18/00* (2006.01)
 *A61B 1/018* (2006.01)

(52) U.S. Cl.
 CPC ...... *A61B 18/1442* (2013.01); *A61B 18/1492* (2013.01); *A61B 1/00071* (2013.01); *A61B 1/018* (2013.01); *A61B 2017/00269* (2013.01); *A61B 2017/2905* (2013.01); *A61B 2017/2929* (2013.01); *A61B 2018/00202* (2013.01); *A61B 2217/007* (2013.01); *A61B 2218/002* (2013.01)

(58) Field of Classification Search
 CPC ............ A61B 17/2812; A61B 17/2816; A61B 17/282; A61B 17/29; A61B 2017/2926; A61B 2017/2939; A61B 2017/2947
 See application file for complete search history.

(56) References Cited

U.S. PATENT DOCUMENTS

| | | | |
|---|---|---|---|
| 6,394,964 | B1 | 5/2002 | Sievert, Jr. et al. |
| 2004/0167514 | A1 | 8/2004 | Okada |
| 2004/0210284 | A1 | 10/2004 | Okada |
| 2005/0228224 | A1* | 10/2005 | Okada ................. A61B 1/00135 600/104 |
| 2006/0270969 | A1 | 11/2006 | Toyonaga et al. |
| 2007/0038213 | A1 | 2/2007 | Machiya et al. |
| 2008/0125809 | A1 | 5/2008 | Suzuki et al. |
| 2011/0282368 | A1 | 11/2011 | Swayze et al. |
| 2014/0350540 | A1 | 11/2014 | Kitagawa et al. |
| 2015/0148803 | A1 | 5/2015 | Kaneko et al. |

FOREIGN PATENT DOCUMENTS

| | | |
|---|---|---|
| EP | 1913876 A1 | 4/2008 |
| EP | 1985252 A1 | 10/2008 |
| EP | 1987795 A1 | 11/2008 |
| EP | 2921120 A1 | 9/2015 |
| EP | 2944280 A1 | 11/2015 |
| JP | S61-111402 U | 7/1986 |
| JP | H11-047135 A | 2/1999 |
| JP | 2002-505904 A | 2/2002 |
| JP | 2004-248911 A | 9/2004 |
| JP | 2005-224426 A | 8/2005 |
| JP | 2006-325785 A | 12/2006 |
| JP | 2007-044393 A | 2/2007 |
| JP | 4315725 B2 | 8/2009 |
| JP | 2011-212450 A | 10/2011 |
| JP | 5754557 B2 | 7/2015 |
| WO | 99/45847 A1 | 9/1999 |
| WO | 2007/017949 A1 | 2/2007 |
| WO | 2014/109181 A1 | 7/2014 |

OTHER PUBLICATIONS

Apr. 5, 2016 International Search Report issued in International Patent Application No. PCT/JP2016/053117.
Jun. 21, 2016 International Search Report issued in International Patent Application No. PCT/JP2016/053106.
U.S. Appl. No. 16/046,593, filed Jul. 26, 2018 in the name of Kuriki.
Aug. 1, 2019 Extended European Search Report issued in European Patent Application No. 16889247.9.
Oct. 1, 2020 Office Action issued U.S. Appl. No. 16/046,593.

\* cited by examiner

ENDOSCOPIC SURGICAL DEVICE

CROSS-REFERENCE TO RELATED APPLICATIONS

This is a continuation of International Application PCT/JP2016/053106, with an international filing date of Feb. 2, 2016, which is hereby incorporated by reference herein in its entirety.

TECHNICAL FIELD

The present invention relates to endoscopic surgical devices.

BACKGROUND ART

A known endoscopic surgical device includes a forceps section that is provided at a distal end of a sheath to be inserted into a channel of an endoscope and that is to be opened and closed by a wire. This endoscopic surgical device delivers a liquid guided via a flow path within the sheath toward a target site from a liquid delivery lumen offset toward the lateral side of the forceps (for example, see Japanese Unexamined Patent Application, Publication No. 2005-224426).

SUMMARY OF INVENTION

An aspect of the present invention provides an endoscopic surgical device comprising: a sheath having a pipe for delivering a liquid and inserted into a channel of an endoscope; a pair of forceps components disposed so as to protrude from a distal end cover provided at a distal end of the sheath; an operable member that is connected to a proximal end of the forceps components, wherein the operable member is configured to open the forceps components when the operable member is moved forward in a longitudinal direction within the pipe of the sheath and close the forceps components when the operable member is moved rearward; and a flow-path formation member that is positioned at proximal end side rather than the forceps components and that is disposed near the distal end within the pipe of the sheath in a rotatable manner about a central axis of the sheath together with the forceps components, wherein the flow-path formation member includes a recess disposed in a direction orthogonal to an opening-closing direction of the forceps components and recessed radially inward, the recess forming a gap between the flow-path formation member and an inner peripheral surface of the distal end cover so as to constitute a liquid delivery hole.

DESCRIPTION OF EMBODIMENTS

An endoscopic surgical device 1 according to an embodiment of the present invention will be described below with reference to the drawings.

Figure 1:
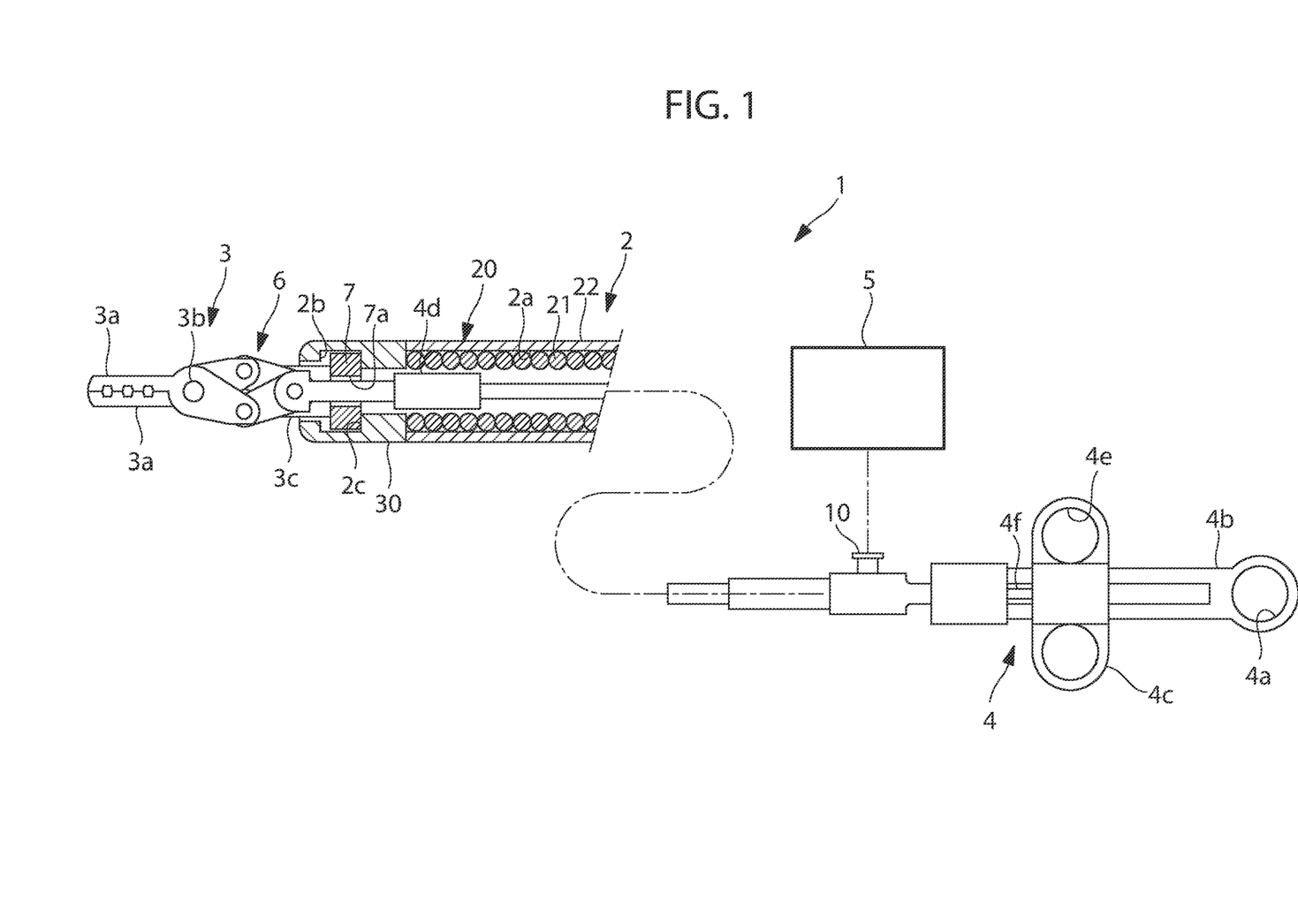
FIG. 1 is an overall configuration diagram in which a distal end section of an endoscopic surgical device according to an embodiment of the present invention is enlarged and in which a part of the endoscopic surgical device is omitted.

For example, the endoscopic surgical device 1 according to this embodiment is a surgical device whose distal end is to be inserted into the body via a channel provided in an insertion section of an endoscope. As shown in FIG. 1, the endoscopic surgical device 1 includes: a flexible sheath 2 having a narrow cylindrical shape insertable into the channel; a forceps section 3 having a pair of forceps components 3a protruding from an opening at the distal end of the sheath 2; an operable section 4 that opens and closes the forceps components 3a by being pushed and pulled at the proximal end of the sheath 2; a wire 4f and an operable member 4d that transmit tension generated by the operable section 4 to the forceps components 3a; and a liquid delivery means 5 that delivers a liquid from the distal end of a distal end cover 30, to be described later, via a flow path (pipe) 2a constituted by an inner hole of the sheath 2.

The sheath 2 includes a sheath body 20 and the distal end cover 30 fixed to the distal end of the sheath body 20. The sheath body 20 includes a coil sheath 21 having an inner diameter larger than the diameter of the wire 4f, and also includes a cylindrical resin casing 22 that covers the outer surface of the coil sheath 21.

The distal end cover 30 is composed of a rigid material, such as metal, and has an outer diameter that is substantially equal to the outer diameter of the resin casing 22.

The distal end of the distal end cover 30 is provided with a collar section 2b that extends radially inward and that reduces the diameter of the flow path 2a. The inner surface of the distal end cover 30 is provided with a stopper section 2c that protrudes radially inward at a position located away from the collar section 2b toward the proximal end by a predetermined distance.

Figure 2:
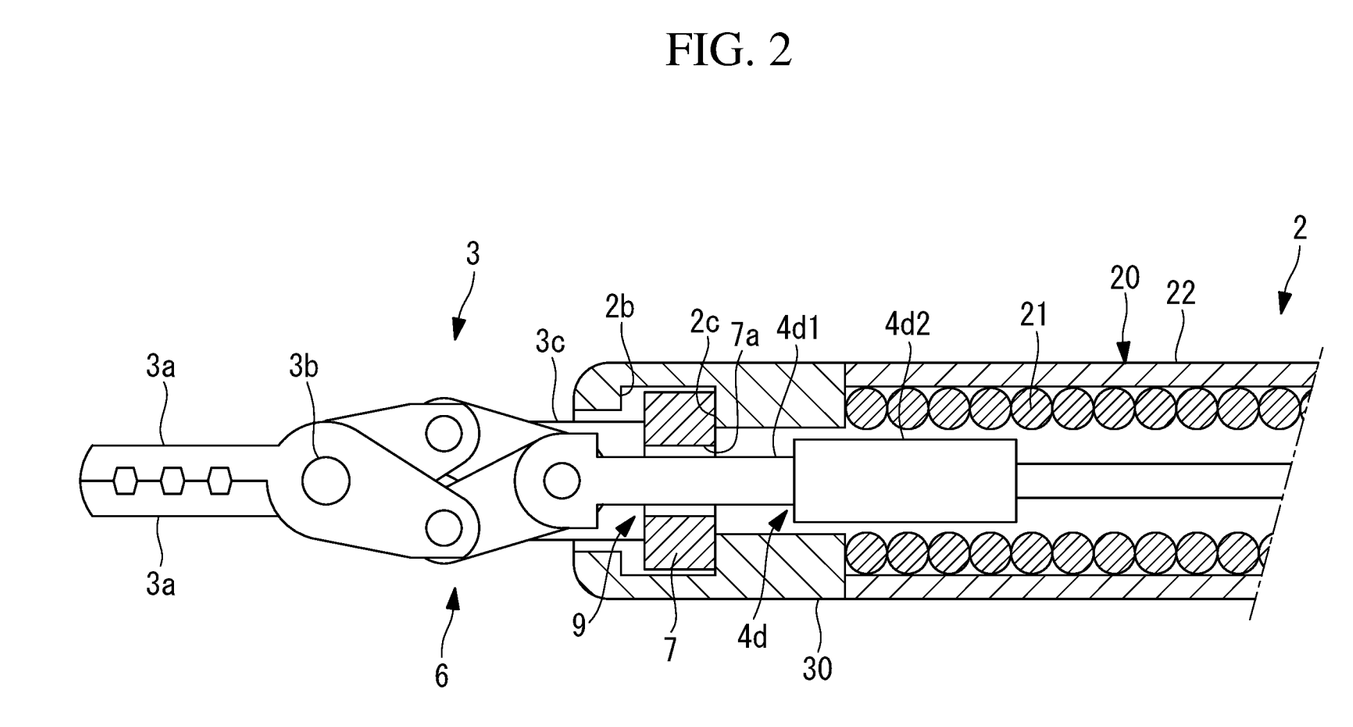
FIG. 2 is an enlarged vertical sectional view illustrating forceps components of the endoscopic surgical device in FIG. 1 in a closed state.
Figure 3:
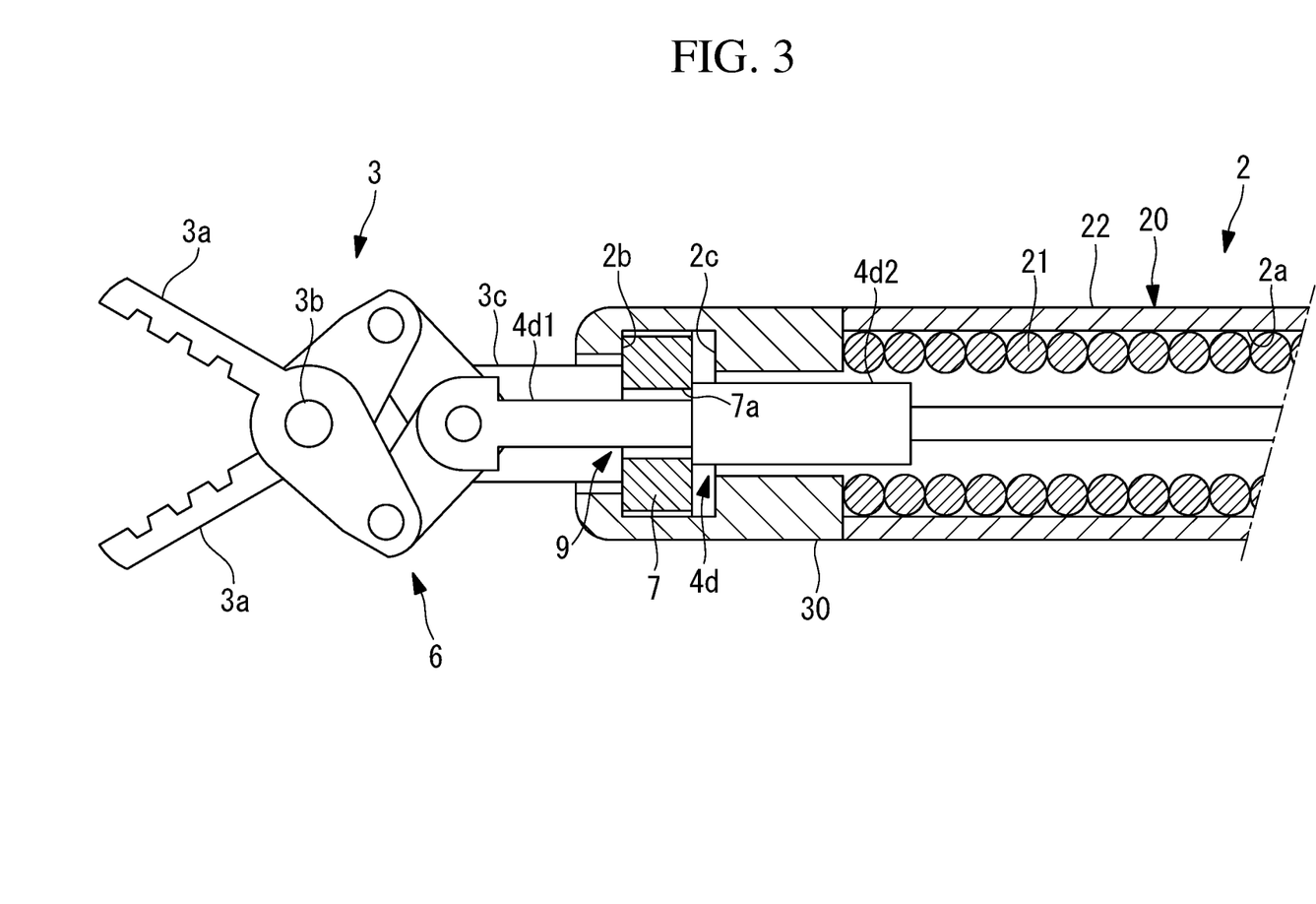
FIG. 3 is an enlarged vertical sectional view illustrating the forceps components of the endoscopic surgical device in FIG. 1 in an open state.

As shown in FIGS. 2 and 3, the forceps section 3 includes a bracket 3c that supports the pair of forceps components 3a in a pivotable manner by means of a pivot shaft 3b. The pair of forceps components 3a are connected to the operable member 4d by a link mechanism 6 provided at the proximal ends of the forceps components 3a. Thus, when the operable member 4d is pulled (retracted) toward the proximal end, the tension of the operable member 4d causes the pair of forceps components 3a to pivot about the pivot shaft 3b in a direction in which the pair of forceps components 3a close, as shown in FIG. 2. When the operable member 4d is pushed (advanced) toward the distal end, the pair of forceps components 3a pivot about the pivot shaft 3b in a direction in which the pair of forceps components 3a open, as shown in FIG. 3.

The width of the forceps components 3a in the opening-closing direction thereof and the width thereof in a direction orthogonal to the opening-closing direction are both set to be smaller than the bracket 3c.

Figure 5:
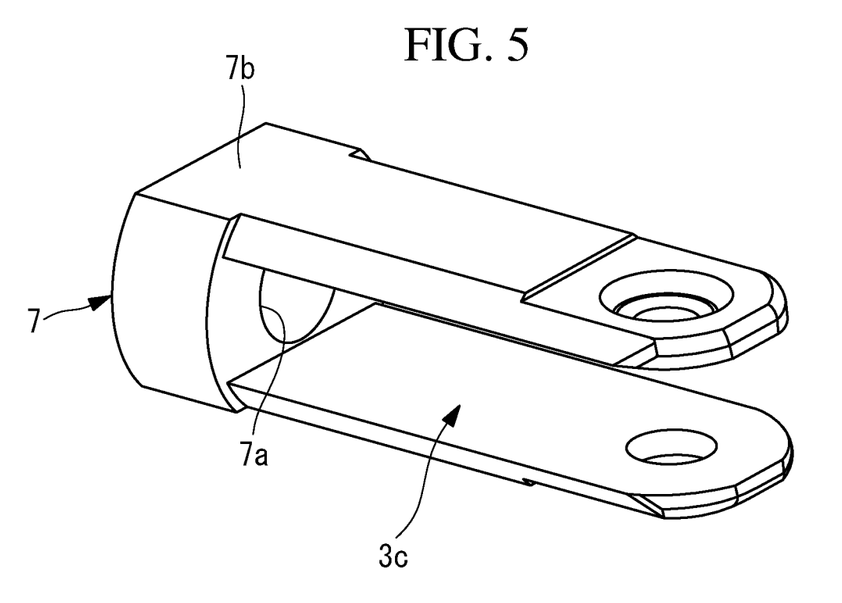
FIG. 5 is a perspective view illustrating a flow-path formation member included in the endoscopic surgical device in FIG. 1.

As shown in FIG. 5, a flow-path formation member 7 having a center hole (through-hole) 7a through which the operable member 4d can extend is integrally fixed to the proximal end of the bracket 3c of the forceps section 3. The flow-path formation member 7 has a disk shape with a diameter slightly smaller than the inner diameter of the distal end cover 30 and larger than the inner diameter of the collar section 2b and includes recesses 7b that are recessed at the opposite sides of the center hole 7a to radial positions sufficiently smaller than the inner diameter of the collar section 2b. The bracket 3c and the flow-path formation member 7 may be independent components and may be fixed to each other by, for example, welding or adhering so long as the two components rotate together.

Figure 6:
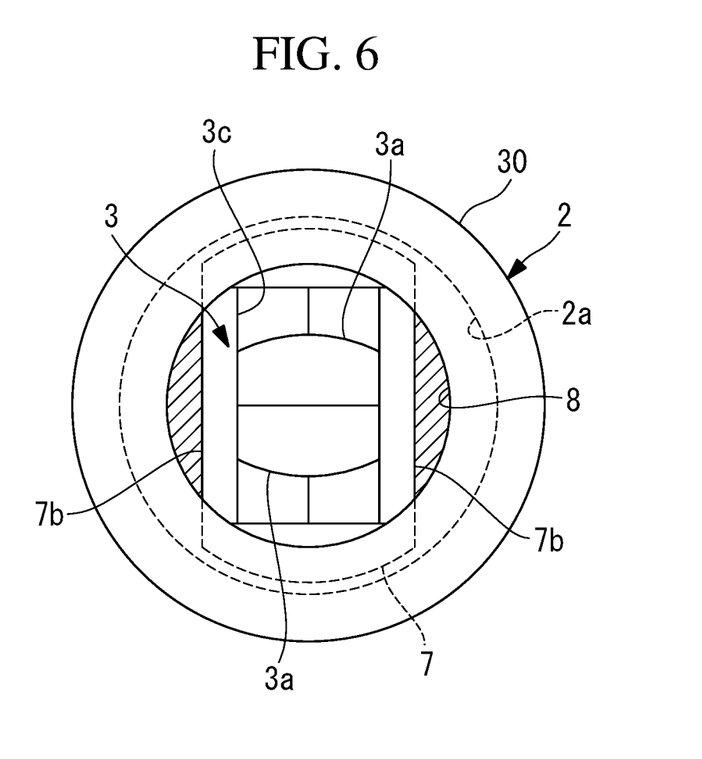
FIG. 6 is a front view of the endoscopic surgical device in FIG. 2.
Figure 7:
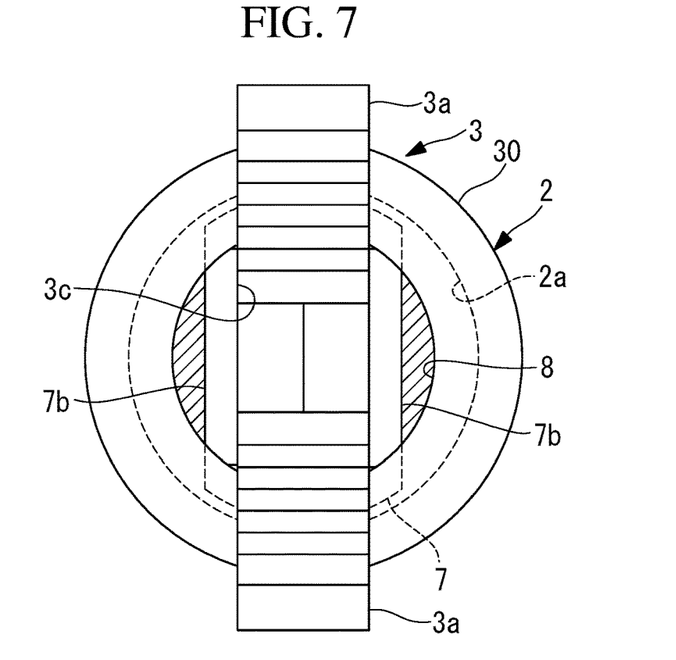
FIG. 7 is a front view of the endoscopic surgical device in FIG. 3.

In the example shown in FIG. 5, the recesses 7b have a shape obtained by cutting out the outer peripheral surface of the flow-path formation member 7 along two flat planes parallel to the axis of the center hole 7a. As shown in FIGS. 6 and 7, the recesses 7b are disposed at positions opposite from each other with the bracket 3c interposed therebetween in a direction orthogonal to the opening-closing direction of the pair of forceps components 3a supported by the bracket 3c. Consequently, gaps between the inner peripheral surface of the distal end cover 30 and the recesses 7b constitute second liquid delivery holes 8 (hatched areas in FIGS. 6 to 8) through which the liquid guided through the sheath 2 is delivered in the forward direction.

Figure 9:
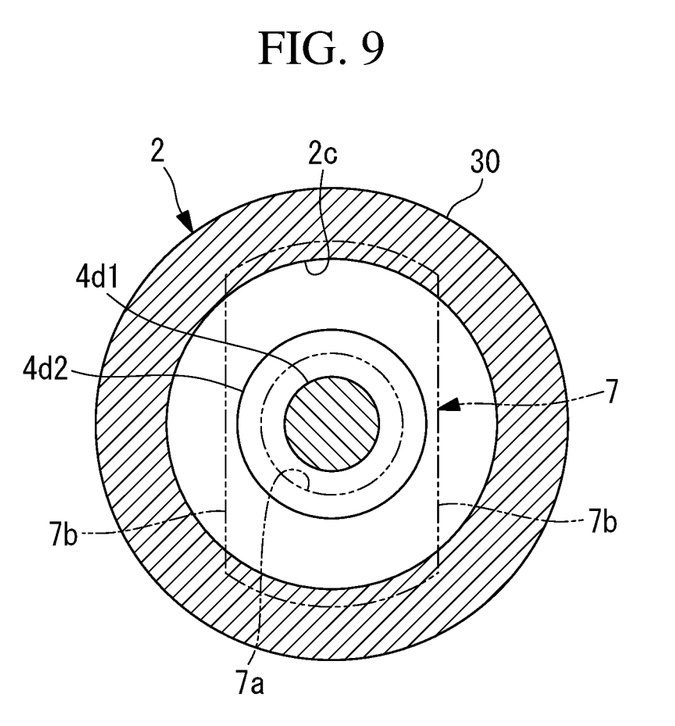
FIG. 9 is a cross-sectional view illustrating the relationship among a stopper section, the flow-path formation member, and an operable member provided within the sheath of the endoscopic surgical device in FIG. 1.

As shown in FIG. 9, the stopper section 2c has a periphery that is smaller than the maximum diameter of the flow-path formation member 7, and protrudes to a radial position larger than the recesses 7b.

The flow-path formation member 7 has a thickness slightly smaller than the distance between the collar section 2b and the stopper section 2c, and is disposed at a position interposed between the collar section 2b and the stopper section 2c. Thus, the flow-path formation member 7 is rotatable about a central axis of the sheath 2.

Figure 4:
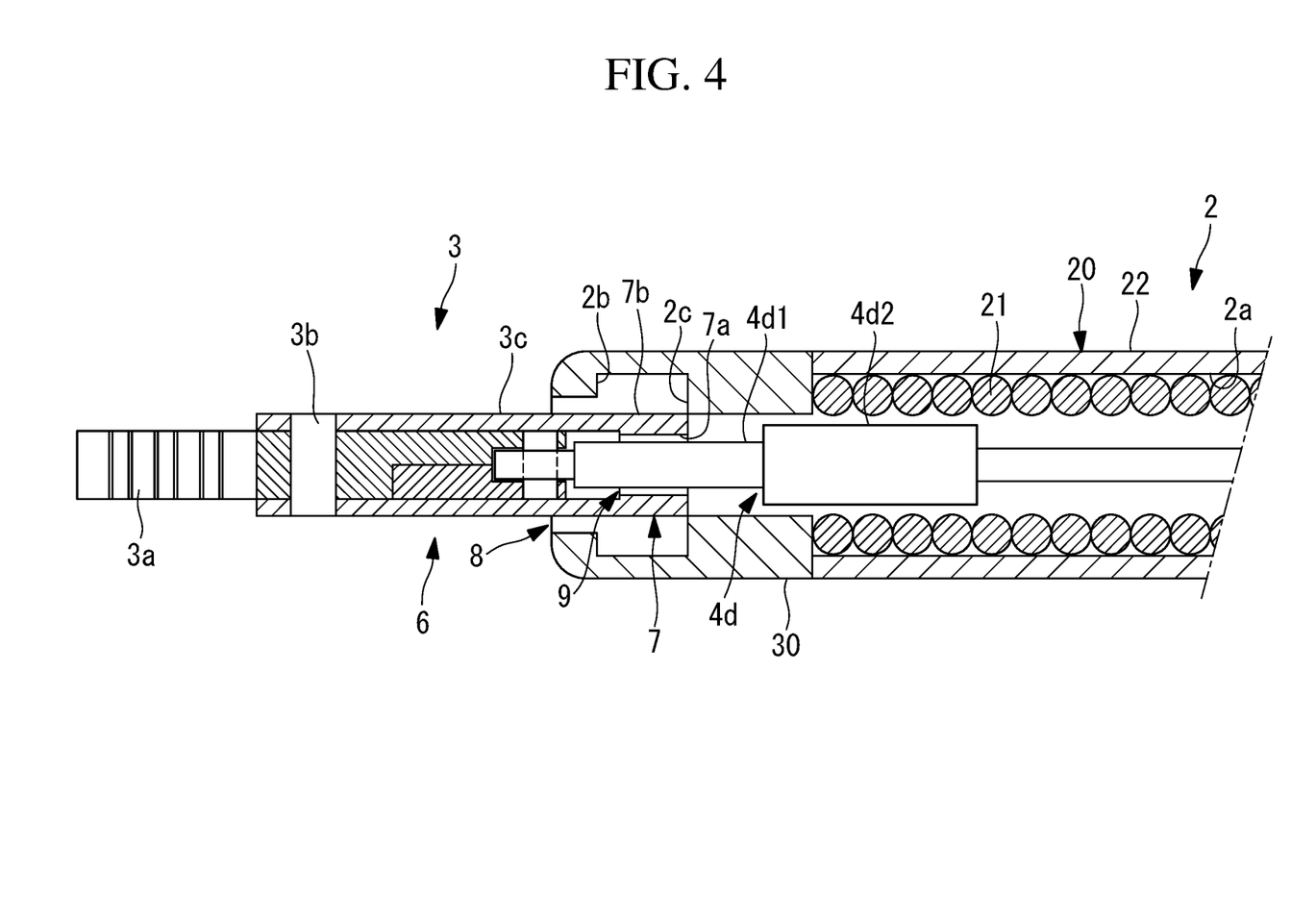
FIG. 4 is an enlarged vertical sectional view taken in a direction orthogonal to an opening-closing direction of the forceps components of the endoscopic surgical device in FIG. 1.

As shown in FIGS. 2 to 4, the operable member 4d includes a small diameter section 4d1 extendable through the center hole 7a of the flow-path formation member 7 and a large diameter section 4d2 disposed toward the proximal end relative to the small diameter section 4d1 and having an outer diameter larger than the center hole 7a. Consequently, a gap between the small diameter section 4d1 of the operable member 4d and the center hole 7a constitute a first liquid delivery hole 9. Then, when the operable member 4d is moved forward, the large diameter section 4d2 of the operable member 4d abuts on the proximal end surface of the flow-path formation member 7 so as to block the first liquid delivery hole 9, as shown in FIG. 3. On the other hand, when the operable member 4d is moved rearward, as shown in FIGS. 2 and 4, the large diameter section 4d2 moves away from the proximal end surface of the flow-path formation member 7 so as to open the first liquid delivery hole 9.

In this embodiment, the operable member 4d, the link mechanism 6, the forceps components 3a, the coil sheath 21, the distal end cover 30, the bracket 3c, and the flow-path formation member 7 are composed of an electrically conductive material through which a high-frequency current can flow.

The operable section 4 includes a handle 4b having a hook hole 4a to be attached to the proximal end of the sheath 2 and a movable section 4c that is movable in the longitudinal direction of the sheath 2 relative to the handle 4b. Reference sign 4e denotes a hook hole provided in the movable section 4c.

When the movable section 4c is moved toward the distal end relative to the handle 4b, a pressing force is transmitted to the link mechanism 6 via the operable member 4d and causes the link mechanism 6 to operate, whereby the forceps components 3a are opened. When the movable section 4c is moved toward the proximal end relative to the handle 4b, a pulling force is transmitted to the link mechanism 6 via the operable member 4d and causes the link mechanism 6 to operate, whereby the forceps components 3a are closed.

A power source (not shown) is connected to the proximal end of the wire 4f, such that a high-frequency current can be applied to the forceps components 3a via the operable member 4d.

The handle 4b is provided with a connection port 10 that communicates with the flow path 2a of the sheath 2.

The liquid delivery means 5 is, for example, a syringe or a pump connected to the connection port 10. By activating the liquid delivery means 5, a liquid, such as a physiological saline solution, can be delivered to the flow path 2a of the sheath 2.

Next, the operation of the endoscopic surgical device 1 according to this embodiment having the above-described configuration will be described.

In order to perform endoscopic submucosal dissection by using the endoscopic surgical device 1 according to this embodiment, the forceps components 3a are closed by operating the operable section 4, as shown in FIG. 2. In this state, the sheath 2 is inserted into the body, starting from the distal end, via the channel in the insertion section of the endoscope until the distal end of the sheath 2 protrudes from the distal end of the insertion section of the endoscope.

Thus, the forceps components 3a disposed at the distal end of the sheath 2 are within the field of view of the endoscope, so that an operator performs treatment while checking an image acquired by the endoscope on a monitor. By applying a high-frequency current via the operable member 4d in the state where the forceps components 3a are closed, the forceps components 3a can be used as a high-frequency knife.

The procedure of the endoscopic submucosal dissection using the endoscopic surgical device 1 according to this embodiment is as follows.

First, a submucosal layer of a site considered to be a lesion to be excised in the endoscopic image displayed on the monitor is pierced with the forceps components 3a in the closed state, and a liquid, such as a physiological saline solution, is injected by means of the liquid delivery means 5, thereby causing the lesion site to bulge.

In this case, since the forceps components 3a are closed, the large diameter section 4d2 of the operable member 4d does not block the first liquid delivery hole 9, as shown in FIGS. 2 and 4. Thus, the liquid guided to the distal end through the flow path 2a of the coil sheath 21 is delivered in the forward direction through both the first liquid delivery hole 9 and the second liquid delivery holes 8. Accordingly, the cross-sectional area of the flow path 2a can be increased, so that a large amount of liquid can be delivered. If a liquid with high viscosity, such as hyaluronic acid, is to be used as the liquid for causing the lesion site to bulge, the above configuration is advantageous in that a large cross-sectional area of the flow path 2a is ensured so that the liquid can be readily delivered.

Subsequently, by using the forceps components 3a in the closed state as a high-frequency knife, an initial dissection process is performed for forming holes at a plurality of locations spaced apart in the circumferential direction in a part of the mucous membrane around the lesion site.

Then, the forceps components 3a in the closed state are inserted into each of the holes formed in the initial dissection process. While a high-frequency current is applied to the forceps components 3a via the operable member 4d, the forceps components are moved in a predetermined dissecting direction intersecting the longitudinal axis. By doing so, the mucous membrane around the lesion site can be excised.

If bleeding occurs during the excision of the mucous membrane around the lesion site, the liquid delivery means 5 is activated so that the liquid is supplied into the flow path 2a of the coil sheath 21 and is used to wash away the blood and to clearly identify the bleeding site, thereby facilitating treatment for stopping the bleeding.

When performing treatment such as excising the dissected mucous membrane, the operator moves the movable section 4c toward the distal end relative to the handle 4b of the operable section 4, so that a pressing force is applied to the link mechanism 6 via the operable member 4d, thereby causing the pair of forceps components 3a to pivot in the opening direction. Then, by applying a twisting force to the operable member 4d, the flow-path formation member 7, the bracket 3c, and the forceps components 3a are rotated about the central axis of the sheath 2 relative to the sheath 2, so that the opening-closing direction of the forceps components 3a can be adjusted.

In this case, since the forceps components 3a are rotated about the central axis of the distal end cover 30 in a state where the forceps components 3a are supported by the distal end cover 30. Thus, the rotating motion of the forceps components 3a is supported by the distal end cover 30, and the opening-closing direction can be stably changed without significantly changing the position of the forceps components 3a, as compared with a case where the entire endoscopic surgical device 1 is rotated.

When the forceps components 3a are disposed in the opening-closing direction in which the mucous membrane can be readily gripped, the movable section 4c is moved toward the proximal end relative to the handle 4b, so that a pulling force is applied to the link mechanism 6 via the operable member 4d, thereby causing the pair of forceps components 3a to pivot in the closing direction. Consequently, treatment such as excising the mucous membrane by gripping it between the pair of forceps components 3a can be performed.

In this case, when the mucous membrane is to be gripped by the forceps components 3a, if the mucous membrane is covered with a liquid, such as blood, it is sometimes not possible to confirm the gripping position by using the endoscope. Thus, it is necessary to clean the mucous membrane in this treatment. Therefore, by activating the liquid delivery means 5, a liquid, such as a physiological saline solution, is delivered via the flow path 2a of the coil sheath 21.

As shown in FIG. 3, in a state where the forceps components 3a are open, the operable member 4d is moved forward so that the first liquid delivery hole 9 is blocked by the large diameter section 4d2. Thus, the liquid is delivered in the forward direction via the second liquid delivery holes 8 alone. By reducing the cross-sectional area of the flow path 2a, the delivery rate of the liquid can be increased.

Because the second liquid delivery holes 8 are constituted by the gaps between the recesses 7b of the flow-path formation member 7 and the inner surface of the distal end cover 30, and the recesses 7b are disposed at positions opposite from each other with the bracket 3c interposed therebetween in the direction orthogonal to the opening-closing direction of the forceps components 3a, the liquid delivered from the second liquid delivery holes 8 is delivered in the forward direction and straight without being hindered by the forceps components 3a in the open state. Consequently, the liquid at the target site can be washed away more reliably.

Figure 8:
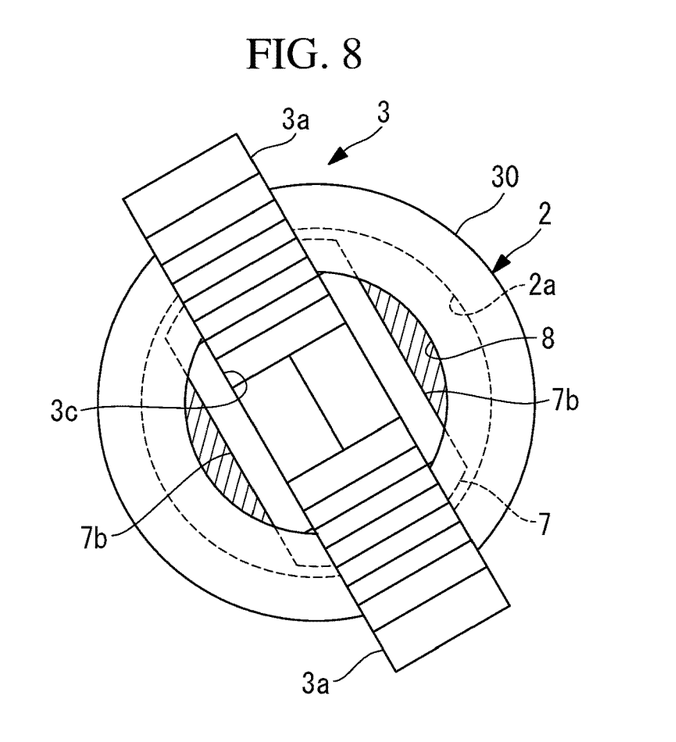
FIG. 8 is a front view illustrating a state where a forceps section of the endoscopic surgical device in FIG. 7 is rotated about a central axis of a sheath.

Because the flow-path formation member 7 is fixed to the bracket 3c, the recesses 7b are always disposed at the positions opposite from each other with the bracket 3c interposed therebetween in the direction orthogonal to the opening-closing direction of the forceps components 3a. This is advantageous in that, even if the opening-closing direction of the forceps components 3a is changed, the liquid to be delivered from the second liquid delivery holes 8 can be delivered in the forward direction and straight, as shown in FIG. 8.

Consequently, the liquid can be delivered to wash the mucous membrane while the forceps components 3a are maintained in a standby state in which they are open for gripping the mucous membrane, and the confirmed mucous membrane can be immediately gripped by using the forceps components 3a.

According to this embodiment, the width of the forceps components 3a in the opening-closing direction thereof and the width of the forceps components 3a in the direction orthogonal to the opening-closing direction are both smaller than the width of the bracket 3c. Therefore, when the forceps components 3a are closed, the forceps components 3a are not in the way of the liquid delivered from the second liquid delivery holes 8, and the current density of the high-frequency current to be applied can be increased at the position of the forceps components 3a. This is advantageous in that the efficiency of dissection can be improved when the forceps components 3a are used as a high-frequency knife.

In the endoscopic surgical device 1 according to this embodiment, the forceps components 3a can be used as a high-frequency knife and as gripping forceps, and can also be used for washing or local injection by delivering a liquid in the forward direction whether the forceps components 3a are in either the closed state or the open state. Therefore, in the above-described endoscopic submucosal dissection, it is not necessary to insert and remove a plurality of surgical devices into and from the channel of the endoscope. This is advantageous in that treatment can be performed from the beginning to the end while the endoscopic surgical device 1 according to this embodiment is maintained in the inserted state.

Accordingly, in the endoscopic surgical device 1 according to this embodiment, the forceps components 3a can be prevented from interfering with the liquid delivery process while the second liquid delivery holes 8 are disposed at the radially outer side of the forceps section 3. Thus, a sufficient liquid delivery amount can be ensured without having to excessively increase the size of the forceps section 3, as compared with a case where the first liquid delivery hole 9 alone is provided. This is advantageous in terms of achieving good insertability into the channel of the endoscope and the patient's body.

In this embodiment, the second liquid delivery holes 8 are provided at the opposite sides of the bracket 3c in the direction orthogonal to the opening-closing direction of the forceps components 3a. Alternatively, only one of the sides may be provided with a second liquid delivery hole 8.

Furthermore, the shape of the recesses 7b constituting the second liquid delivery holes 8 is not limited to the shape obtained by cutting out the outer peripheral surface of the disk-shaped flow-path formation member 7 along flat planes, and may alternatively be another freely-chosen shape.

As a result, the following aspect is read from the above described embodiment of the present invention.

An aspect of the present invention provides an endoscopic surgical device comprising: a sheath having a pipe for delivering a liquid and inserted into a channel of an endoscope; a pair of forceps components disposed so as to protrude from a distal end cover provided at a distal end of the sheath; an operable member that is connected to a proximal end of the forceps components, wherein the operable member is configured to open the forceps components when the operable member is moved forward in a longitudinal direction within the pipe of the sheath and close the forceps components when the operable member is moved rearward; and a flow-path formation member that is positioned at proximal end side rather than the forceps components and that is disposed near the distal end within the pipe of the sheath in a rotatable manner about a central axis of the sheath together with the forceps components, wherein the flow-path formation member includes a recess disposed in a direction orthogonal to an opening-closing direction of the forceps components and recessed radially inward, the recess forming a gap between the flow-path formation member and an inner peripheral surface of the distal end cover so as to constitute a liquid delivery hole.

The above aspect may further include a bracket that supports the forceps components in an openable-closable manner, wherein the flow-path formation member is fixed to the proximal end of the bracket.

According to this aspect, in a state where the sheath is inserted into the channel of the endoscope and the forceps section protruding from the distal end cover provided at the distal end of the sheath protrudes from the distal end of the endoscope, the operable member is operated at the proximal end of the sheath, so that the pair of forceps components of the forceps section can be opened and closed, whereby a target site can be treated. When a liquid is supplied from the proximal end of the sheath via the pipe provided in the sheath, the liquid is delivered in the forward direction toward the target site through the liquid delivery hole formed by the gap between the recess provided in the flow-path formation member and the inner peripheral surface of the distal end cover.

In this case, when the flow-path formation member at the distal end of the sheath is rotated about the central axis of the sheath, the bracket fixed to the flow-path formation member and the forceps components supported by the bracket in an openable-closable manner are also rotated about the central axis of the sheath. Thus, the forceps components are rotated using the distal end cover as a guide, so that the opening-closing direction of the forceps components can be stably changed while the forceps components are maintained at a fixed position.

Moreover, in this case, since the recess is disposed in the direction orthogonal to the opening-closing direction of the forceps components relative to the bracket that supports the forceps components in an openable-closable manner, the liquid can be delivered in the forward direction without being hindered by the forceps components during the opening-closing operation of the forceps components. Thus, the delivered liquid is not hindered by the forceps components even immediately before the target site is to be gripped by opening the forceps components, so that body fluid, such as blood, at the target site can be washed away efficiently.

In the above aspect, the recess may include recesses provided at opposite sides of the bracket in the direction orthogonal to the opening-closing direction of the forceps components.

Accordingly, the liquid can be delivered in the forward direction toward the target site through the liquid delivery holes provided at the opposite sides of the bracket. The force applied to the sheath as a result of the liquid delivery process is evenly applied thereto with respect to the central axis of the sheath, so that the sheath can be made stable during the liquid delivery process. Moreover, even if the flow of the liquid from one of the liquid delivery holes is hindered by an obstacle ahead, the washing process can still be performed by using the liquid delivered through the other liquid delivery hole.

Furthermore, in the above aspect, the forceps components and the operable member may each be composed of an electrically conductive material capable of flowing a high-frequency current.

Accordingly, with the high-frequency current applied via the operable member, the forceps section can be used as a high-frequency knife. Treatment that involves gripping with the forceps section, washing or local injection by delivering the liquid, or treatment that involves cutting with a high-frequency knife can be performed in a switchable manner in a state where the endoscopic surgical device is left inserted in the channel of the endoscope.

Furthermore, in the above aspect, a width of the forceps components in the opening-closing direction is smaller than the bracket.

Furthermore, in the above aspect, a width of the forceps components in the direction orthogonal to the opening-closing direction is smaller than the bracket.

Accordingly, the density of the high-frequency current in the forceps section can be increased, thereby facilitating a cutting process. Moreover, it is possible to prevent a hindrance in the direction of the delivered liquid.

REFERENCE SIGNS LIST

1 endoscopic surgical device
2 sheath
2a flow path (pipe)
3 forceps section
3a forceps components
3c bracket
4d operable member
7 flow-path formation member
7b recess
8 second liquid delivery hole (liquid delivery hole)
9 first liquid delivery hole (liquid delivery hole)
30 distal end cover

The invention claimed is:
1. An endoscopic surgical device comprising:
a sheath having a flow path for delivering a liquid outside of the sheath via an opening in a distal end of the sheath;
a pair of forceps components disposed so as to protrude from the distal end of the sheath;

an elongate member that is connected to a proximal end of the forceps components and is inserted into the opening so as to be spaced apart from an inner peripheral surface of the sheath that forms the opening, the elongate member being configured to rotate around a central axis of the sheath within the flow path of the sheath; and a flow-path formation member that is disposed in a rotatable manner about the central axis of the sheath together with the forceps components, wherein:
the flow-path formation member includes a guide surface disposed between the inner peripheral surface of the sheath and the elongate member in at least one of: (i) a direction orthogonal to an opening-closing direction of the forceps components, and (ii) the distal end of the sheath, the inner peripheral surface of the sheath and the guide surface define a first liquid delivery hole, and the device is configured to deliver the liquid through the first liquid delivery hole to outside of the distal end of the sheath on an outer side of the forceps components, the sheath includes a distal end cover provided at a distal end thereof; and the flow-path formation member includes a distal facing surface that abuts against an inner peripheral surface of the distal end cover when the forceps components are open.

2. The endoscopic surgical device according to claim 1, further including a bracket that supports the forceps components in an openable-closable manner,
wherein the flow-path formation member is fixed to a proximal end of the bracket.

3. The endoscopic surgical device according to claim 2, wherein:
the flow-path formation member further comprises a second guide surface, and
the guide surface and the second guide surface are provided at opposite sides of the bracket in the direction orthogonal to the opening-closing direction of the forceps components.

4. The endoscopic surgical device according to claim 2, wherein the forceps components and the elongate member are each composed of an electrically conductive material capable of flowing a high-frequency current.

5. The endoscopic surgical device according to claim 2, wherein a width of the forceps components in the opening-closing direction is smaller than the bracket.

6. The endoscopic surgical device according to claim 2, wherein a width of the forceps components in the direction orthogonal to the opening-closing direction is smaller than the bracket.

7. The endoscopic surgical device according to claim 1, wherein:
the flow-path formation member includes a through-hole through which the elongate member extends,
a diameter of the through-hole of the flow-path formation member is larger than at least a portion of an outer diameter of the elongate member, and
the through-hole and the elongate member form a second liquid delivery hole through which the device is configured to deliver the liquid.

8. The endoscopic surgical device according to claim 1, wherein the elongate member is configured to open the forceps components when the elongate member is moved forward in a longitudinal direction within the flow path of the sheath and close the forceps components when the elongate member is moved rearward.

9. The endoscopic surgical device according to claim 1, wherein:
the flow-path formation member is movable in a longitudinal direction with respect to the sheath between a proximal position and a distal position.

10. The endoscopic surgical device according to claim 1, wherein:
the distal end cover includes a stopper that protrudes radially inward and is disposed on a proximal end side of the flow-path formation member.

11. The endoscopic surgical device according to claim 1, wherein the flow-path formation member is composed of an electrically conductive material.

12. An endoscopic surgical device comprising:
a sheath having a flow path for delivering a liquid outside of the sheath via an opening in a distal end of the sheath;
a pair of forceps components disposed so as to protrude from the distal end of the sheath;
an elongate member that is connected to a proximal end of the forceps components and is inserted into the opening so as to be spaced apart from an inner peripheral surface of the sheath that forms the opening, the elongate member being configured to rotate around a central axis of the sheath within the flow path of the sheath; and
a flow-path formation member that is disposed in a rotatable manner about the central axis of the sheath together with the forceps components,
wherein:
the flow-path formation member includes a guide surface disposed between the inner peripheral surface of the sheath and the elongate member in at least one of: (i) a direction orthogonal to an opening-closing direction of the forceps components, and (ii) the distal end of the sheath,
the inner peripheral surface of the sheath and the guide surface define a first liquid delivery hole,
the device is configured to deliver the liquid through the first liquid delivery hole to outside of the distal end of the sheath on an outer side of the forceps components,
the sheath includes a distal end cover provided at a distal end thereof; and
the distal end cover includes a collar that protrudes radially inward from an inner surface of the distal end cover to so as to reduce a diameter of the flow path, and the guide surface of the flow-path formation member is spaced radially inward from a radially innermost surface of the collar.

13. An endoscopic surgical device comprising:
a sheath that has a flow path for delivering a liquid and is configured to be inserted into a channel of an endoscope, the sheath including a distal end cover provided at a distal end thereof;
a pair of forceps components disposed so as to protrude from the distal end cover;
an elongate member that is connected to a proximal end of the forceps components, the operable elongate member being configured to open the forceps components when the elongate member is moved forward in a longitudinal direction within the flow path of the sheath, and close the forceps components when the elongate member is moved rearward; and a flow-path formation member that is positioned at a proximal end side of the forceps components and is disposed within a distal end of the flow path of the sheath in a rotatable manner about a central axis of the sheath together with the forceps components, wherein:
the flow-path formation member includes a recessed surface that is recessed radially inward with respect to an inner peripheral surface of the distal end cover in a direction orthogonal to an opening-closing direction of the forceps components, the recessed surface forming a gap between the flow-path formation member and the inner peripheral surface of the distal end cover so as to constitute a liquid delivery hole, and the flow-path formation member is movable in the longitudinal direction with respect to the sheath.

14. An endoscopic surgical device comprising:
a sheath that has a flow path for delivering a liquid and is configured to be inserted into a channel of an endoscope, the sheath including a distal end cover provided at a distal end thereof;
a pair of forceps components disposed so as to protrude from the distal end cover;
an elongate member that is connected to a proximal end of the forceps components, the elongate member being configured to open the forceps components when the elongate member is moved forward in a longitudinal direction within the flow path of the sheath, and close the forceps components when the elongate member is moved rearward; and
a flow-path formation member that is positioned at a proximal end side of the forceps components and is disposed within a distal end of the flow path of the sheath in a rotatable manner about a central axis of the sheath together with the forceps components, wherein:
the flow-path formation member includes a recessed surface that is recessed radially inward with respect to an inner peripheral surface of the distal end cover in a direction orthogonal to an opening-closing direction of the forceps components, the recessed surface forming a gap between the flow-path formation member and the inner peripheral surface of the distal end cover so as to constitute a liquid delivery hole, and the elongate member includes a first section and a second section having a larger diameter than the first section, and the second section is configured to abut against a proximal facing surface of the flow-path formation member so as to block a through hole extending through the flow-path formation member when the forceps components are open.

\* \* \* \* \*